(12) United States Patent
DeGraaf et al.

(10) Patent No.: US 11,406,802 B2
(45) Date of Patent: *Aug. 9, 2022

(54) STENT TRIMMING DEVICES AND METHODS

(71) Applicant: Boston Scientific Scimed, Inc., Maple Grove, MN (US)

(72) Inventors: Kimberly DeGraaf, Holden, MA (US); Peter J. Pereira, Mendon, MA (US); Manuel Teixeira, Boston, MA (US); William A. Sturos, Elk River, MN (US); Jefferson R. Alpizar, Heredia (CR); Jozef Slanda, Milford, MA (US); Mark Hera, Holden, MA (US); Michael S. H. Chu, Brookline, MA (US); David Salto, Hopedale, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 188 days.

This patent is subject to a terminal disclaimer.

(21) Appl. No.: 16/708,749

(22) Filed: Dec. 10, 2019

(65) Prior Publication Data

US 2020/0114131 A1 Apr. 16, 2020

Related U.S. Application Data

(63) Continuation of application No. 15/837,596, filed on Dec. 11, 2017, now Pat. No. 10,532,196.

(60) Provisional application No. 62/433,138, filed on Dec. 12, 2016.

(51) Int. Cl.
*A61F 2/95* (2013.01)
*A61F 2/04* (2013.01)
*A61M 27/00* (2006.01)
*B21F 45/00* (2006.01)
*A61B 17/32* (2006.01)
*B23D 29/02* (2006.01)

(52) U.S. Cl.
CPC ... *A61M 27/008* (2013.01); *A61B 17/320016* (2013.01); *A61F 2/04* (2013.01); *A61F 2/95* (2013.01); *B21F 45/008* (2013.01); *A61B 2017/32004* (2013.01); *A61F 2/9517* (2020.05); *A61F 2002/047* (2013.01); *A61F 2002/9534* (2013.01); *A61F 2250/0007* (2013.01); *A61F 2250/0098* (2013.01); *A61M 2209/04* (2013.01); *B23D 29/023* (2013.01)

(58) Field of Classification Search
CPC .............. A61F 2/95; A61F 2/04; A61M 27/00
USPC ....................................... 623/1.11
See application file for complete search history.

(56) References Cited

U.S. PATENT DOCUMENTS 6,036,708 A * 3/2000 Sciver ............ A61B 17/320783
606/159
8,906,085 B2 * 12/2014 Rice ........................ A61F 2/915
623/1.29

(Continued)

*Primary Examiner* — Suzette J Gherbi
(74) *Attorney, Agent, or Firm* — Seager, Tufte & Wickhem, LLP

(57) ABSTRACT

Devices and methods for trimming a stent to a desired length with an outer tube and an inner tube having a distal end and a diameter configured to receive a portion of the stent in excess of the desired length. The inner tube may move within the outer tube and the distal end may include an end effector configured to trim the portion from the stent while the device and stent are within a patient.

12 Claims, 14 Drawing Sheets

(56) References Cited

U.S. PATENT DOCUMENTS

| | | | |
|---|---|---|---|
| 2003/0033016 A1* | 2/2003 | Dees, Jr. | A61F 2/0095 |
| | | | 623/10 |
| 2003/0153968 A1* | 8/2003 | Geis | A61F 2/07 |
| | | | 623/1.11 |
| 2008/0051705 A1* | 2/2008 | Von Oepen | A61F 2/954 |
| | | | 604/101.01 |
| 2010/0043199 A1* | 2/2010 | Rice | A61F 2/91 |
| | | | 29/527.2 |
| 2016/0256212 A1* | 9/2016 | Recber | B26B 17/00 |
| 2018/0361118 A1* | 12/2018 | Cully | A61M 25/0084 |
| 2019/0099280 A1* | 4/2019 | Ben Muvhar | A61F 2/04 |
| 2019/0328560 A1* | 10/2019 | Saranin | A61F 2/95 |

* cited by examiner

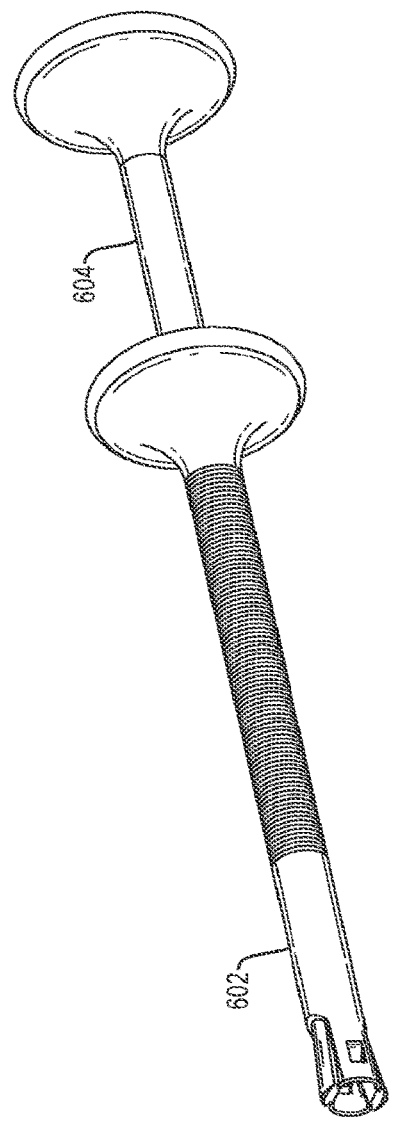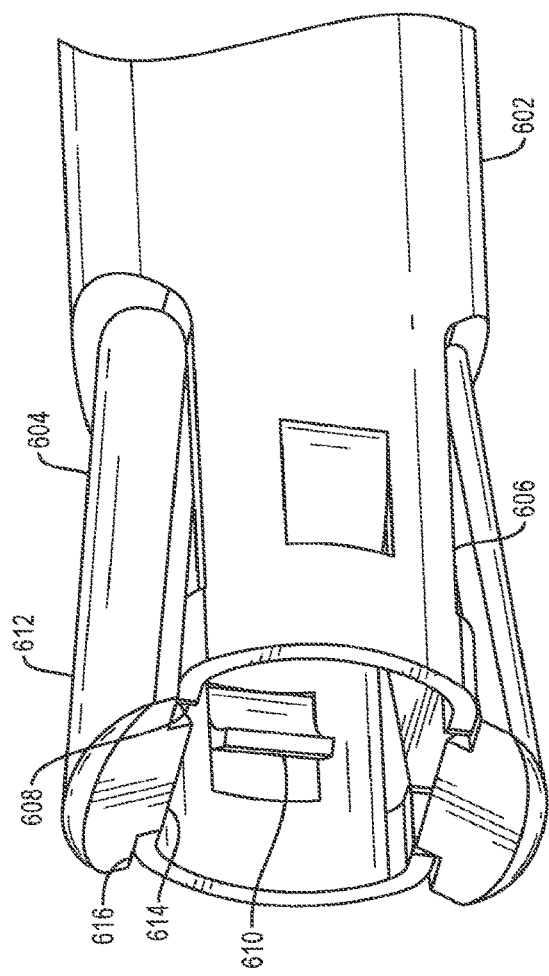
FIG. 6A
FIG. 6B

STENT TRIMMING DEVICES AND METHODS

PRIORITY

This application is a continuation of U.S. patent application Ser. No. 15/837,596, filed Dec. 11, 2017, which claims the benefit of priority under 35 U.S.C. § 119 to U.S. Provisional Patent Application Ser. No. 62/433,138, filed Dec. 12, 2016, which is incorporated by reference herein in its entirety and for all purposes.

FIELD

The present disclosure relates generally to medical devices for trimming medical stents to a desired length while the stent is within the body of a patient, and more particularly to devices and methods for trimming stents placed in the ureter to facilitate drainage from the kidney to the bladder.

BACKGROUND

Medical devices developed for implantation or insertion into patients are known for various purposes including stenting, drainage, etc., of lumens, tracts, vessels, and cavities within the body. As an example, polymeric ureteral stents are widely used to facilitate drainage in the upper urinary tract (e.g., drainage from the kidney to the bladder), for example, following ureteroscopy, endourerotomies, and endopyelotomy for ureteral strictures, as well as in other instances where ureteral obstruction may occur.

An exemplary stent 10 of this type is illustrated in FIG. 1. The stent 10 has a proximal end 10p and a distal end 10d. It is a tubular polymer extrusion having a shaft 12, a distal renal retention structure (e.g., renal "pigtail" 14), and a proximal retention structure (e.g., bladder "pigtail" 16). These retention structures prevent upward migration of the stent toward the kidney or downward migration of the stent toward the bladder. Once properly deployed in the ureter, the stent 10 provides ureteral support and allows the passage of urine. The stent 10, as exemplified by FIG. 1, may further be provided with any one or more of the following: (a) a tapered tip 11, to aid insertion, (b) multiple side ports 18 (one numbered), which are typically arranged in a spiral pattern down the length of the body to promote drainage, (c) graduation marks 25 (one illustrated), which are normally used for visualization by the physician to know when the appropriate length of stent has been inserted into the ureter, and (d) a suture 22, which aids in positioning and withdrawal of the stent.

During placement, such ureteral stents 10 are typically placed over a urology guide wire, through an access sheath, and advanced into position with a pusher. Once the distal end of the stent is advanced into the kidney/renal calyx, the guide wire is removed, allowing the pigtails 14, 16 to form in the kidney 19 and bladder 20, as shown in FIG. 2. The renal pigtail 14 of the stent may be closed or tapered on the end, depending on the method of insertion (e.g., the use of a guide wire or otherwise). As shown in FIG. 2, the stent 10 extends through the ureteral orifice 21a and into the bladder 20. The other ureter entering bladder 20 through the opposite ureteral orifice 21b is not shown.

These types of implanted medical devices may be associated with patient discomfort or pain after being positioned within the body, for example, in regard to ureteral stents, pain and/or discomfort in the bladder and flank area after insertion. Another potential issue is that various applications and anatomies require medical devices of different diameters and lengths, e.g., differences in individual ureteral anatomies require different diameters and lengths between the end retention structures of ureteral stents. Consequently, hospitals and other facilities inventory stents of different diameters and for each diameter, stents of different lengths, in some cases as much as six stents of different lengths for each diameter.

Generally, a physician must estimate ureter length before beginning a procedure. If the estimate is near the end of a particular length range of stents that are kept on hand, it is possible to select a stent that is slightly too long or too short. However, that fact may not be ascertainable until the stent has been implanted. The procedure for correcting any incorrect selection involves removing that stent and placing a longer or shorter stent in the ureter thereby complicating the procedure and potentially increasing patient trauma.

Variable length stents include offset, planar, or nautilus coils at one or both of the end retention structures that can be unwound to increase or decrease the effective length between the structures. Another ureteral stent example includes a stent with multi-turn coils at the bladder end that may be clipped off outside of the body when the length of the stent has been estimated by the physician.

Although these examples may reduce inventory requirements, excess retention structure left in the bladder may occupy a considerable volume which may increase a risk of tissue irritation. Additionally, stents clipped to length outside of the body prior to placement may ultimately result in a length that is too short, requiring a new stent to be used, or too long, in which case the excess material and irritation concerns remain. Therefore, there exists a need for medical devices and methods to trim a stent within the patient to ensure that it is sized accurately and consistently without excess volume leftover that may cause irritation.

SUMMARY

The present disclosure, in its various aspects, meets an ongoing need in the medical field, such as the field of ureteral stents, for stent trimming devices and methods which ensure a proper stent length during stent positioning within a patient.

A device for trimming a proximal end of a stent to a desired length may include an outer tube with an inner tube having a proximal end, a distal end, and an inner diameter configured to receive an outer diameter of at least a portion of the proximal end of the stent in excess of the desired length. The inner tube may be movably disposed within the outer tube. The distal end of the inner tube may include an end effector configured to trim the portion from the stent while the device and stent are within a patient.

An embodiment of the disclosure may include an inner tube configured to receive the portion of the stent only within the end effector at the distal end of the inner tube. An embodiment may include an inner tube configured to receive the portion of the stent along the entire length of the inner tube. An embodiment may include an end effector with an opened and closed configuration. An embodiment may include an end effector that has two or more arms biased away from a longitudinal axis of the device in the opened position. An embodiment may include an outer tube that movably encompasses the end effector in the closed configuration of the inner tube. An embodiment may include a stent that is a ureteral stent, where the proximal end includes a distal tip with a bladder retention segment, and the trimmed stent portion comprises a portion of the distal tip.

An embodiment of the disclosure for trimming a proximal end of a stent to a desired length may include an outer tube and an inner tube movably disposed within the outer tube. The inner tube may have a proximal end and a distal end. The distal end may be configured to trim a portion of the proximal end of the stent in excess of the desired length in vivo.

An embodiment of the present disclosure may include a tip extended from a distal end of the outer tube. The tip may include a window having an opening along a side surface of the outer tube substantially perpendicular to a longitudinal axis of the outer tube. The window may be configured to receive at least the portion of the stent. The inner tube may have a sharpened edge at the distal end of the inner tube, whereby relative movement of the inner tube with respect to the outer tube engages the sharpened edge with the tip.

An embodiment of the present disclosure may include a tip with a post disposed within the tip. The post may have a beveled proximal face angled toward the window opening.

An embodiment of the present disclosure may include a pair of inner arms extended from the distal end of the inner tube and biased toward each other in the direction of the longitudinal axis. The pair of inner arms may each include a first inward facing tab with a pair of notches. An embodiment may include a pair of outer arms extended from the outer tube and biased toward each other in the direction of the longitudinal axis. The pair of outer arms may each include a pair of second inward facing tabs configured to engage a notch on the first inward facing tabs of each inner arm on opposing sides of the inner tube. The outer arms may include a pair of fingers extending inwardly from the pair of outer arms.

An embodiment may include a distal end of the inner tube with three splayed arms, each with a sharpened edge pointed substantially inward toward a longitudinal axis of the inner tube. An embodiment may include a first aperture near a distal end of the outer tube that is substantially perpendicular to a longitudinal axis of the outer tube. The inner tube may include a second aperture near the distal end of the inner tube that is substantially perpendicular to a longitudinal axis of the inner tube with at least one sharp edge, the inner tube and outer tube being rotatable with respect to each other to engage the inner tube edge. An embodiment may include an inner tube with a concentric internal shelf on the inside of the inner tube of a smaller diameter than the inner tube and further. A third tube may be removably disposed within the distal end of the inner tube. The third tube may include an opening configured to receive at least the portion of the stent to be trimmed and a plurality of blades at a distal end of the third tube that are concentrically spaced apart from each other around the opening, and wherein the outer tube tapers down to a smaller diameter at a distal end. The inner tube may have outer threads on an outer surface at the distal end of the inner tube and wherein the outer tube has inner threads on an inner surface at the distal end of the outer tube that engage the outer threads on the inner tube.

A method of trimming a stent of the present disclosure may include introducing a stent into a patient. The method may include introducing a stent trimming device into the patient. The method may include measuring a portion of the stent to be trimmed. The method may include trimming the portion within the patient with the stent trimming device. The method may include measuring the portion through an aperture of the device. The method may include trimming the portion by moving an inner tube relative to an outer tube of the device. The method may include introducing the stent and introducing the stent trimming device simultaneously.

BRIEF DESCRIPTION OF THE DRAWINGS

Non-limiting examples of the present disclosure are described by way of example with reference to the accompanying figures, which are schematic and not necessarily drawn to scale. In the figures, each identical or nearly identical component illustrated is typically represented by a single numeral. Not every component is labeled in every figure, nor is every component of each embodiment of the disclosure shown where illustration is not necessary to allow those of skill in the art to understand the disclosure. In the figures:

FIG. 6A illustrates an example embodiment of a medical device for trimming a stent.

FIG. 6B illustrates a closer view of the stent trimming device of FIG. 6A.

It is noted that the drawings are intended to depict only typical or exemplary embodiments of the disclosure. Accordingly, the drawings should not be considered as limiting the scope of the disclosure. The disclosure will now be described in greater detail with reference to the accompanying drawings.

DETAILED DESCRIPTION

Devices, systems and methods in accordance with various embodiments of the present disclosure include medical devices capable of trimming a stent in vivo. The devices include an inner elongated tubular member having a lumen extending along a length thereof. The devices also include an outer elongated tubular member having a lumen extending along a length thereof. The members may be semi-flexible along the length. The distal end of the devices is configured to trim a stent in vivo in order to achieve a stent of a desired length.

Various embodiments according to the present disclosure are described below. As used herein, "proximal end" refers to the end of a device that lies closest to the medical professional or outside the urethral exit (downstream) in the case of a ureteral stent, and "distal end" refers to the end of an implanted or positioned device or object that lies furthest from the medical professional or urethral exit (upstream) when used in the context of a ureteral stent.

The various embodiments of adjustable length medical devices (e.g., stents) which may be trimmed according to embodiments of devices and methods of the present disclosure, including as described above and below, may have any of the following features. Devices, particularly in the context of a ureteral stent, may have an outer diameter of about 3 French to about 9 French, including any half or whole size within that range, and may have an inner diameter of about 0.038 inches (about 0.097 cm) to accommodate the profile of standard medical guidewires within the lumen of the tubular member. Embodiments of ureteral stents useful for devices and methods of the present disclosure may have an adjustable length of about 10 cm to about 35 cm as measured between the retention members.

Figure 1:
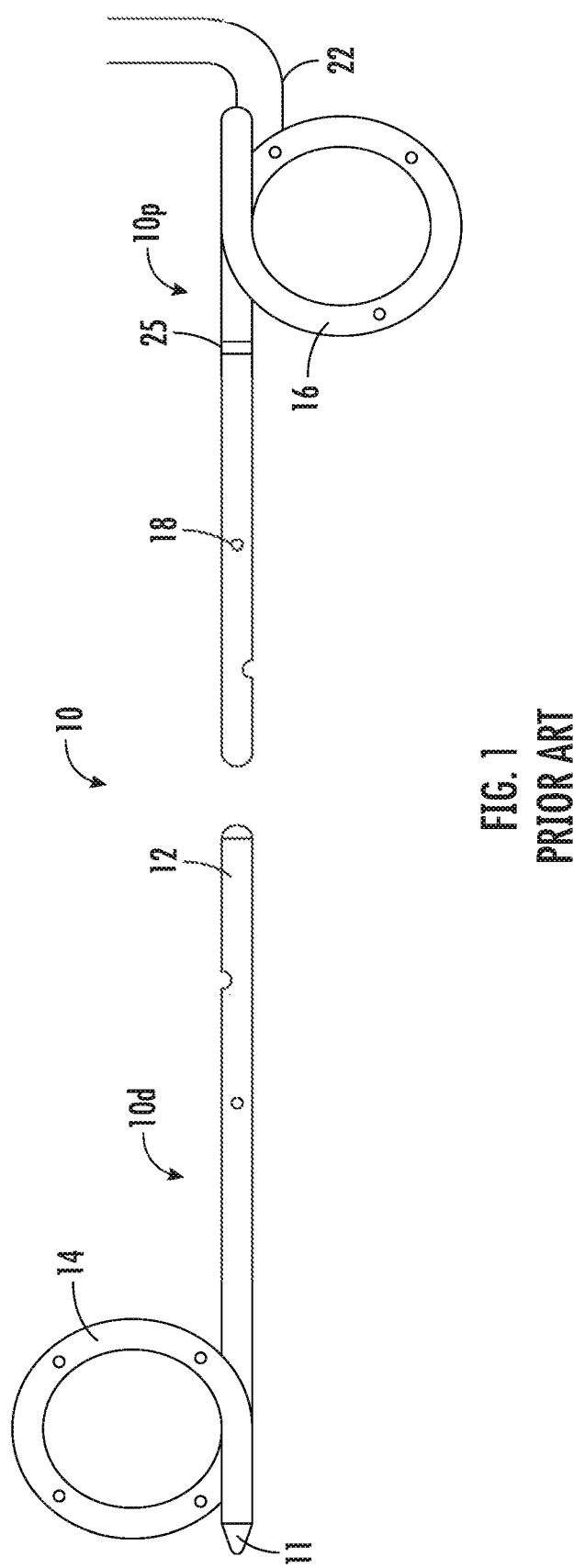
FIG. 1 is an illustration of a ureteral stent, according to the prior art.
Figure 2:
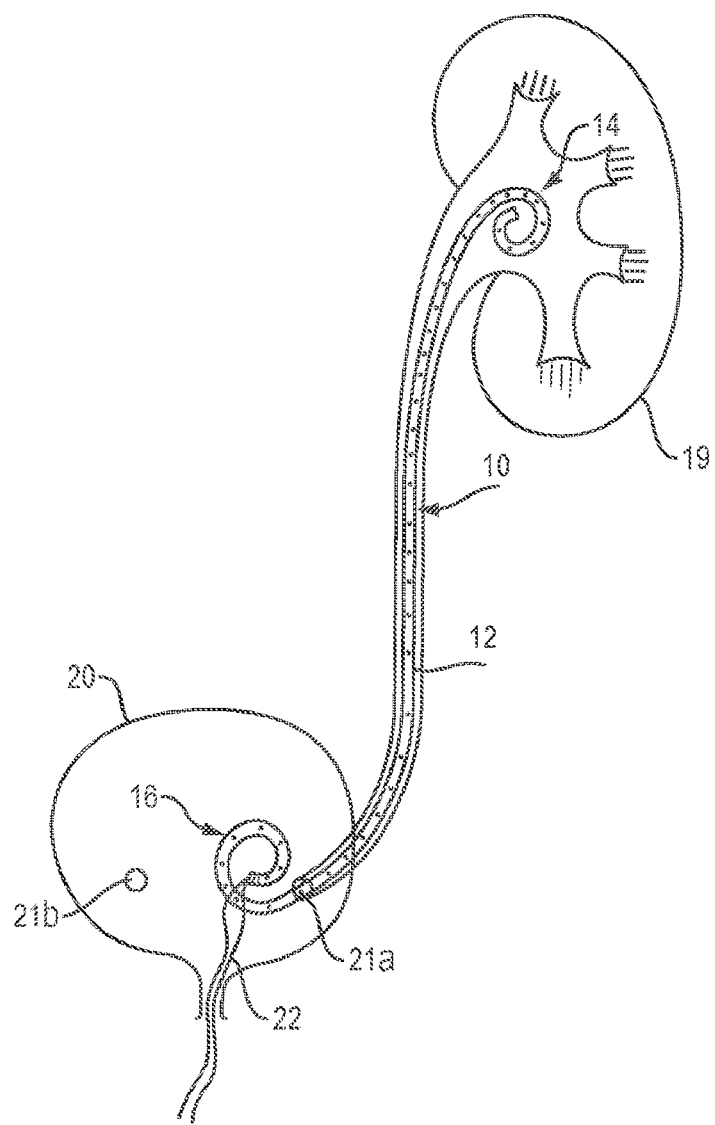
FIG. 2 is an illustration of a prior art ureteral stent, like that of FIG. 1, positioned in the body.

In a ureteral stent implantation procedure, a guidewire is fed into the bladder, then into the ureter, past the renal pelvis, and into the kidney. A stent may then be guided over the guidewire along the same path so that it may be positioned from the kidney to the bladder along the ureter. Once in position, the guidewire may be withdrawn, leaving the stent implanted in the patient as illustrated in the prior art of FIG. 2. It is desirable for the patient to receive an implanted stent of comfortable length. Too long of a stent may cause undesirable irritation to the patient. Too short, and the stent may migrate out of position and cease to function properly. Adult patients typical require ureteral stents with a length of about 10 cm (3.9 in) to about 35 cm (13.8 in.) as measured between the retention members. A stent with retention members (e.g. pigtails) may add about 10 cm to about 15 cm of additional length. Rather than estimate stent lengths, it would be preferable for a medical professional to trim a stent in vivo within a patient to tailor the length to their body's dimensions.

The stents with which various embodiments of trimming devices of the present disclosure may be used, alone or as system or kit along with a stent, may contain one or more optional additives, for example, selected from therapeutic agents, radiopaque agents, colorants, other optional additives such as plasticizers and extrusion lubricants, and combinations of the above, among others, in amounts effective to serve their intended purposes. Where used, such optional additives may be present, for example, in polymeric, among others, or in coatings applied to the polymeric materials, or both.

Radiopaque agents facilitate viewing of the medical device during insertion of the device and at any point while the device is implanted. Among radiopaque agents useful in the medical devices of the present disclosure are included bismuth salts such as bismuth subcarbonate, bismuth oxychloride, bismuth trioxide, barium sulfate, tungsten, and mixtures thereof. More specific examples of such radiopaque agents include tungsten, platinum, tantalum, iridium, gold, or other dense metal, barium sulfate, bismuth subcarbonate, bismuth trioxide, bismuth oxychloride, metrizamide, iopamidol, iothalamate sodium, iodomide sodium, and meglumine, among others. Where present, the radiopaque agent is typically present in an amount of from about 10% to about 40% (including 10% to 15% to 20% to 25% to 30% to 35% to 40%, with 15-30% being more typical). Additionally or alternatively, the polymeric material or additive material choice, as well as extrusion technique, may be optimized to enhance device contrast using ultrasound imaging. The incorporation of sonographic agents, in addition to or as an alternative to radiopaque agents, such as contrast beads or foams, among other examples, facilitate viewing of the medical device under ultrasonic imaging during insertion of the device and at any point while the device is implanted. One skilled in the art can readily determine an appropriate radiopaque and sonographic agent content to achieve the desired visibility. The polymer materials described may be mixed with the radiopaque and/or the sonographic agents above, or a colorant. A colorant may be used as a visual cue to a medical professional about the location of the medical device in the patient. Graduated markings on the stent may assist the medical professional with measuring a length of stent to trim.

Figure 3:
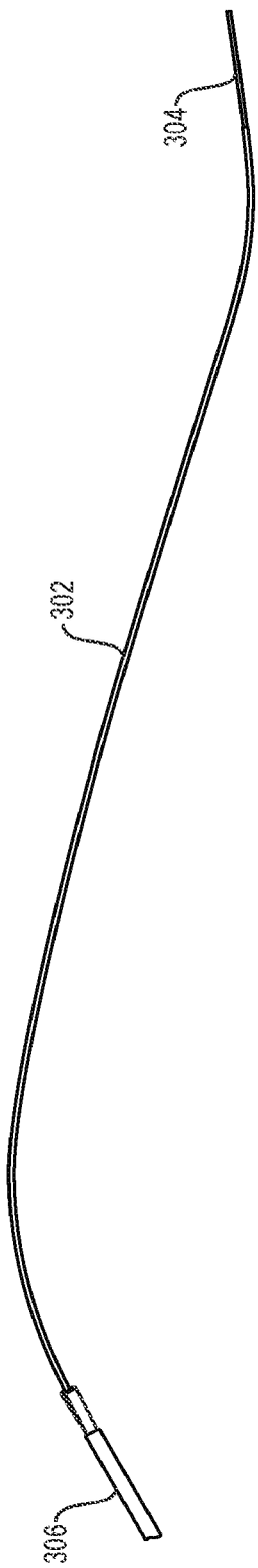
FIG. 3 illustrates an example embodiment of a medical device for trimming a stent, wherein the device is shown engaging a stent for trimming.

With reference to FIG. 3, for example, a stent 302 may be guided over a guidewire 304 thereby straightening any retention members of the stent along the wire within a patient. The stent slides along the guidewire, alone or is carried on a catheter or other delivery device that the wire extends through. The guidewire, if used alone, may be sufficiently stiff to hold the retention members straight while the guidewire is in the lumen of the stent. An outer pusher member slidably coaxial with an inner member of a delivery device, or with a wire if used alone, may be used to abut the proximal end of the stent and push the stent distally. A radiopaque or sonographic band, filler or other marker as part of the pusher and/or delivery device allows a medical professional to view the pusher and/or device on a fluoroscope or using ultrasound. Additionally, if the stent is radiopaque or sonovisible, placement of the stent in the patient may be confirmed by viewing the stent on a fluoroscope or by using ultrasound. Once positioned at the distal end of the placement point, the guidewire alone or in conjunction with a delivery device, if used, is withdrawn from the lumen of the distal (or kidney, in the case of a ureteral stent) retention member. If a pusher is used, the pusher holds the stent in place while the guidewire or guidewire and inner member of the delivery device is removed. The shape-memory of the retention member allows the retention member to return to its shape memory configuration, such as a pigtail coil.

As the guidewire and/or delivery device is withdrawn into, for example, the bladder in the case of a ureteral stent, the medical professional sights the bladder retention member and proximal portion including any graduated markings corresponding to incremental portions along the length thereof. If included, the graduated marking that approximates the desired length of the stent extending along the ureter at the placement point of the proximal retention member, e.g., the bladder retention member, may be identified.

Once the desired length is identified (with or without the aid of graduated markings), the stent may be adjusted by trimming the stent at the incremental portion that corresponds to the excess of the desired length. The medical professional may movably operate the inner and outer tubes of the trimming device by grabbing the handle or handles of the device and moving, sliding, and/or rotating the tubes. Trimming may be done in the absence of graduated markings, as long as there is a way to determine the amount of excess stent to be trimmed from the desired length. Divots, holes, perforations, or the like, within and along the stent wall may make the stent easier to trim. The trimming may be done with a medical device or with a tool that is integrated therewith, while the stent is on a guidewire or within a delivery device, in accordance with embodiments described herein. Various embodiments of trimming devices in accordance with the present disclosure are contemplated as suitable to engage and trim a stent or other medical device at a desired length, utilizing some form of trimming mechanism with a sharpened edge and applied pressure, such as cutting blades, cutting wires, heated wires or blades, grasping, punching, crimping or pinching mechanisms, or the like. Heated tools may include a mold to form a taper on the end of the tubular member after the incremental portion is trimmed from the remainder of the stent.

Trimming may be accomplished while a stent is still in a straightened configuration on the guidewire or delivery device, or after a guidewire alone or in conjunction with a delivery device, if used, is withdrawn from the lumen of a proximal (or bladder, in the case of a ureteral stent) retention member and the retention member assumes its shape memory form, such as a multi-turn planar coil. The trimmed incremental portion may be removed from the bladder by various means.

A tapered tip on the distal retention member can facilitate inserting a stent through the passages of a patient's body. Additionally, a suture on a stent can be used to reposition the stent (by pulling on it) when inserting the stent, and a suture may be used to remove the stent from the patient after some period of use, provided the suture is secured to a portion of the stent above any incremental portion that may be trimmed. When the stent is to be removed, the medical professional may pull on the suture to remove the stent. However, other means may be used to remove the stent.

A medical device for trimming a stent 306 may be guided over the guidewire 304 so that the distal end of the device 306 may receive any excess portion of the stent 302 that the medical professional determines is additional unnecessary length of the stent 302. An end effector of the distal end of the device 306 may be configured to trim the excess portion of the stent 302 of a desired length of the stent 302. The excess portion of stent 302 may be withdrawn from the patient along with the device 306.

Alternatively, with reference to FIG. 3, the medical device for trimming a stent may be guided over the guidewire 304 and the stent 302 may be guided over the guidewire 304 and through the device 306. The stent 302 may be fed out of the distal end of the device 306. A desirable length of stent 302 may be measured by the medical professional, and any excess portion of stent 302 may be separated by the trimming mechanism of the distal end of device 306. The excess portion of stent 302 may be withdrawn from the patient along with the device 306.

A medical professional may measure a tailored length of a stent for each patient before trimming away any excess length. This may be performed while the medical professional is positioning the stent via fluoroscopy. A tip of the medical device may be radiopaque so that the medical professional may visually see via fluoroscopy where the trimming tip of the device is located within the patient to trim the excess stent at an appropriate length. Alternatively, a ureteroscope or other type of camera may be used by the medical professional to measure and trim an appropriate length of the stent.

Figure 4A:
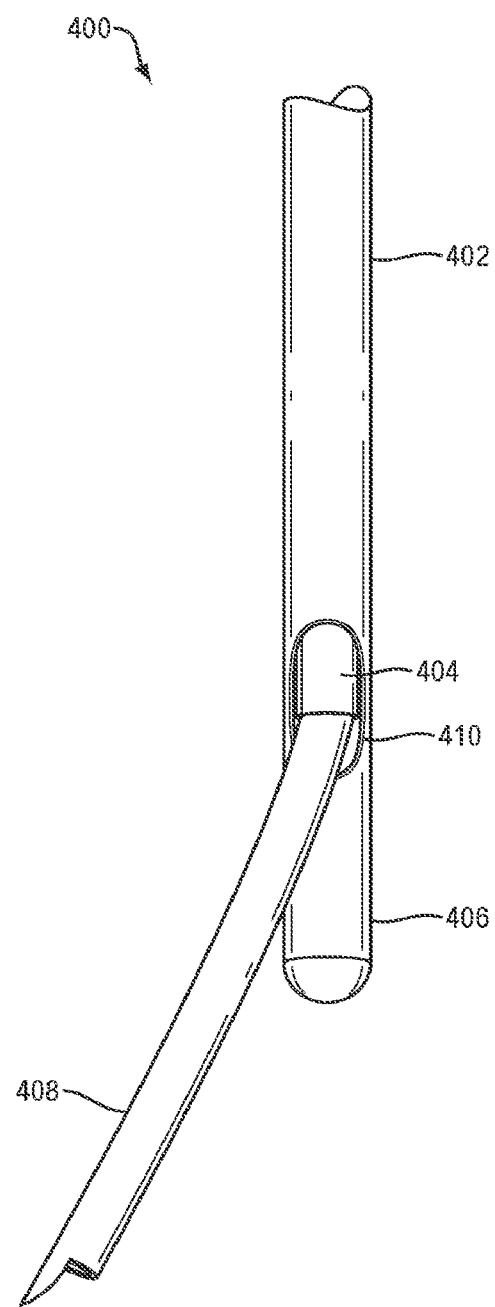
FIG. 4A illustrates an example embodiment of a medical device for trimming a stent.

With reference to FIG. 4A, an embodiment of the disclosure may include an outer tube 402 with an inner tube 404 that can movably slide within the outer tube 402. The distal end of the outer tube 402 may have a tip 406 extended from the distal end of the outer tube 402. The tip 406 may include a window 410 having an opening along a side surface of the outer tube 402 substantially perpendicular to a longitudinal axis of the outer tube 402. The window 410 is configured to receive at least a portion of the stent. The inner tube 404 may slide into the tip 406. The window 410 of outer tube 402 may create an area of egress in the outer tube for a guidewire (not shown) and/or a stent 408.

Figure 4B:
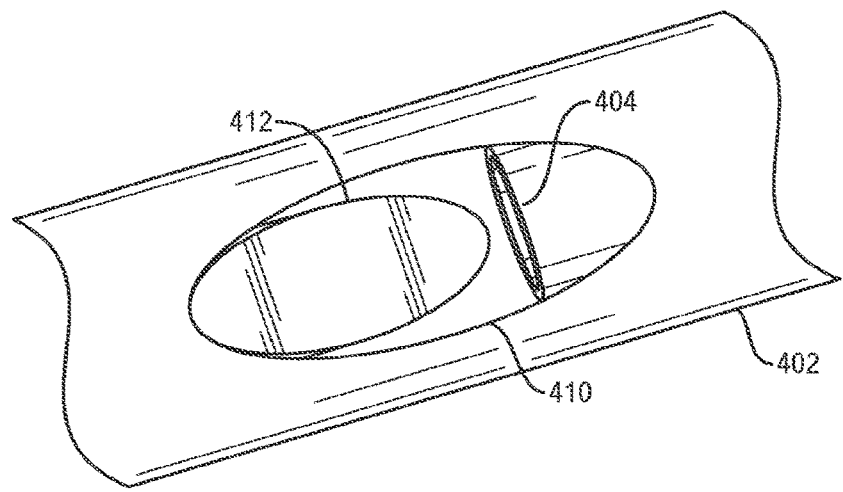
FIGS. 4B-4C illustrate a closer view of the window for stent and guidewire ingress and egress of the example embodiment of a medical device for trimming a stent of FIG. 4A.
Figure 4C:
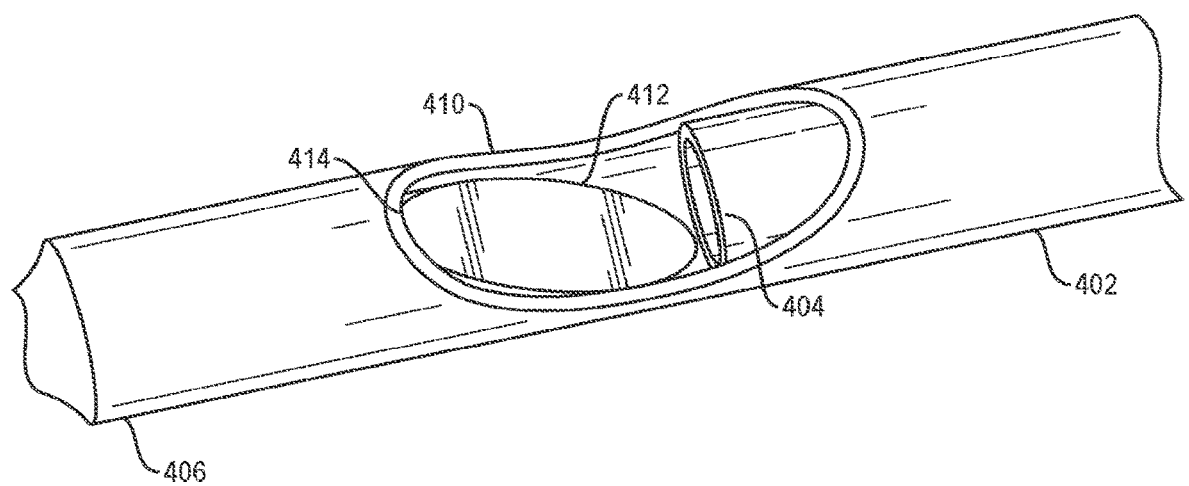

Referring to FIG. 4B, the outer tube 402 may have a bevel 412 with a face that is angled at about 45° to the direction of the window 410, or angled at different angles as desired. A guidewire and/or stent may be deflected out and away from outer tube 402 by being directed tangentially by the face of the bevel 412. The length of the stent 408 may be measured by translating the stent 408 within the inner tube 404. Additionally or in the alternative, the entire medical device 400 may be translated in relation to the stent 408 in order to measure an appropriate length of the stent 408 to be positioned and implanted in the patient. Once measured, the stent 408 may be trimmed by translating the inner tube 404 distally in relation to the outer tube 402 into the tip 406. Referring to FIG. 4C, the inner tube 404 may slide over the bevel 412 and inside the edge 414 of the window 410. The bevel 412 prevents the stent (not shown) from being pushed into the tip 406 from the compressing force of the translation of the inner tube 404. The bevel 412 and the edge 414 assist the inner tube 404 in trimming the stent (not shown).

Figure 4D:
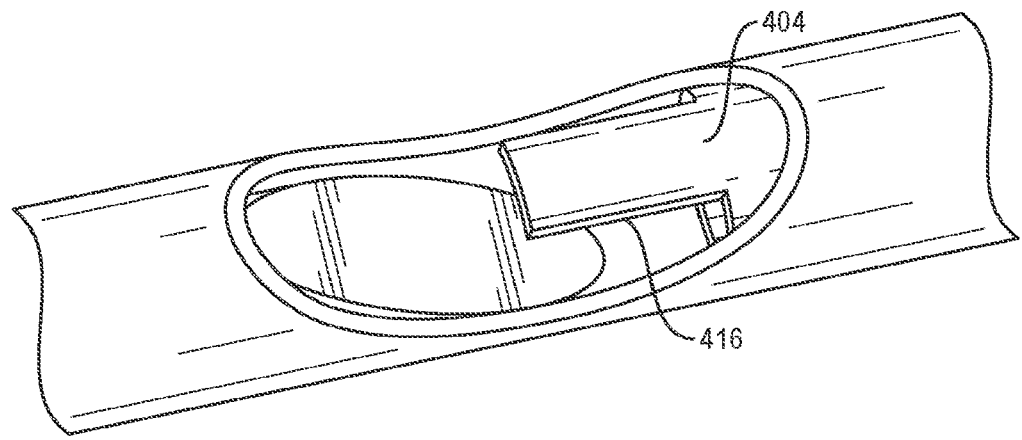
FIG. 4D illustrates an example embodiment of a medical device for trimming a stent.
Figure 4E:
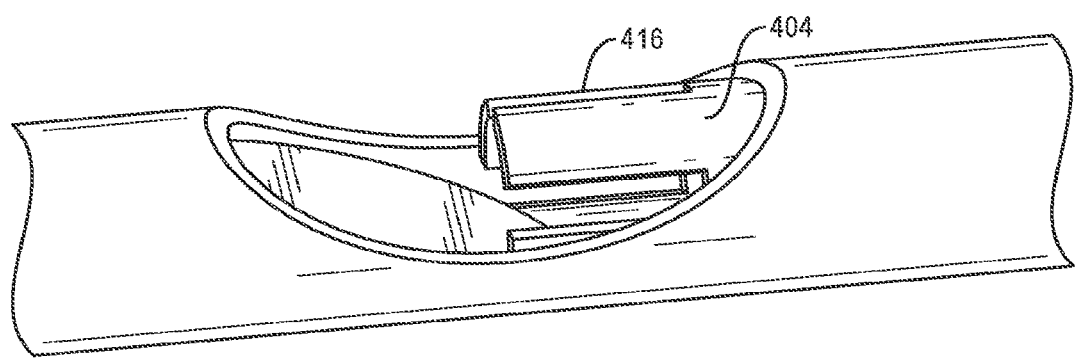
FIG. 4E illustrates an example embodiment of a medical device for trimming a stent.

Referring to FIGS. 4D and 4E, a cutting edge or edges 416 may exist on the distal end of the inner tube 404 and/or in addition to a cutting edge or edges on the bevel 412. Trimming of the stent 408 may be performed by the translation of the inner tube 404 and/or the rotation of the inner tube 404 relative to the outer tube 402.

Figure 5A:
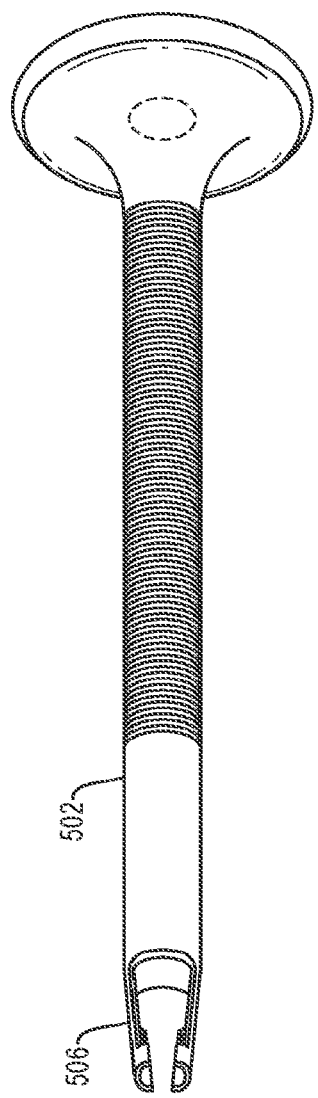
FIG. 5A illustrates a top view of an outer tube of an example embodiment of a medical device for trimming a stent.
Figure 5B:
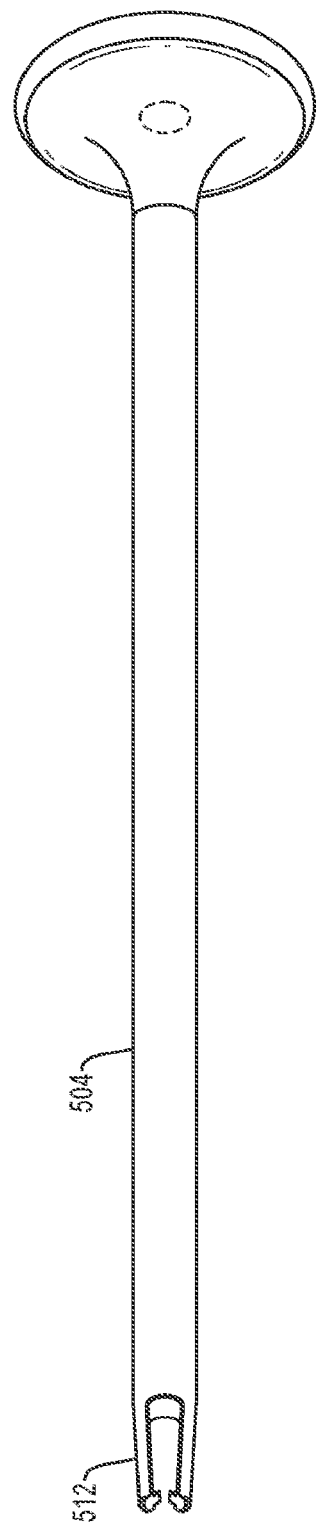
FIG. 5B illustrates a side view of an inner tube of an example embodiment for trimming a stent.

Referring to FIGS. 5A and 5B, an example embodiment of a trimming device of the disclosure may include an outer tube 502 with outer arms 506 at the distal end. The arms 506 are biased toward each other. Inner tube 504 may have inner arms 512 that are biased toward each other. Each of the inner arms 512 may include a first inward facing tab with a pair of notches, while each pair of outer arms 506 may include a pair of second inward facing tabs configured to engage a notch on the first inward facing tabs of each inner arm 512 on opposing sides of the inner tube 504. The outer arms 506 may also include a pair of fingers extending inwardly. The manner in which these inner arms 512 and outer arms 506 interact will be discussed with reference to FIGS. 6A and 6B. Inner tube 604 may movably slide into outer tube 602 such that the inner arms 612 and the outer arms 606 engage each other. When the arms engage each other, the inner arms 612 are deflected outwards when the outer tabs 608 engage the notches 616 on the inner tabs 614. Additionally, as the inner arms 612 engage the outer arms 606, the outer arms are deflected outwards when the inner tabs 614 engage the outer tabs 608. With the inner arms 612 and outer arms 606 in an outwardly deflected state, a stent (not shown) may be received by the distal end of the tubes. A medical professional may measure out an appropriate length of stent to be positioned within a patient before deciding to trim the excess amount of the stent. When the medical professional moves the inner tube 604 proximally, the notches 616 slide over the outer tabs 608 until they disengage from the outer tabs 608 completely. At this point the inner arms 612 and outer arms 606 transition into a collapsed state since the arms are biased towards each other. As the inner arms 612 collapse towards each other, inner tabs 614 pinch the stent at a location between the fingers 610 of the outer tube 602. These fingers 610 may also pinch the stent in the collapsed state of the tubes. As the inner tube 604 is translated proximally, tensile stress is applied to the stent at the pinching point between the four edges of the inner tabs 614 and the fingers 610. Continued application of tensile stress to the stent will trim the excess portion of the stent. The excess portion of the stent and the inner tube 604 may be drawn proximally through the outer tube 602 and away from the stent's positioning site. Gaps may be allowed between each of the inner tabs 614 and the fingers 610 wide enough for a guidewire to remain without being pinched in the collapsed state.

Figure 7A:
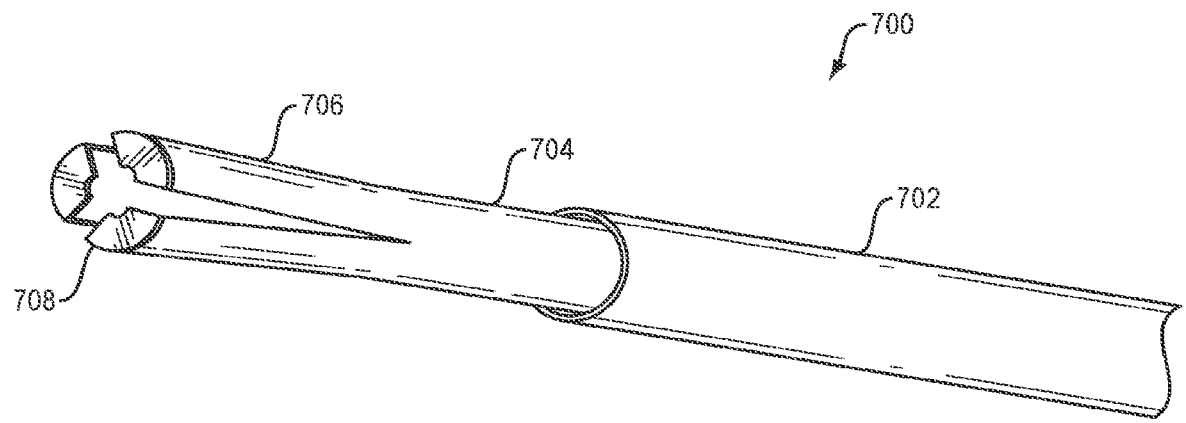
FIG. 7A illustrates an example embodiment of a medical device for trimming a stent.
Figure 7B:
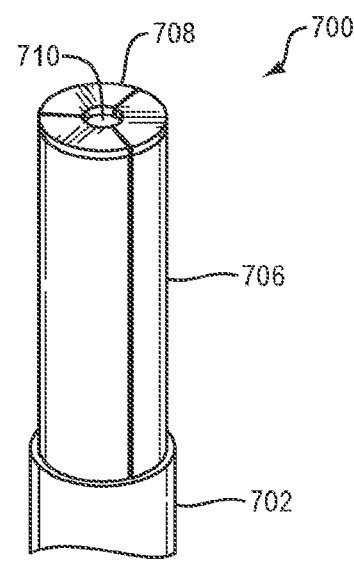
FIG. 7B illustrates a closed configuration of the stent trimming device of FIG. 7A.

Referring to FIGS. 7A and 7B, an embodiment of a trimming device of the present disclosure may include an outer tube 702 and an inner tube 704 that may movably translate into the outer tube 702. The inner tube 704 may have three arms 706 splayed at its distal end. The three arms 706 may each have a sharpened edge, e.g., blade 708, that is directed inwardly. The splayed arms 706 will close towards each other when the inner tube 704 is translated relative to the outer tube 702. In the inner tube's 704 closed state, a window 710 is vacant to allow for the device 700 to be guided along a guidewire (not shown). When the device 700 reaches the stent (not shown), the inner tube 704 may be translated through the outer tube 702 distally so that the members 706 splay open to receive an excess portion of the stent. The inner tube 704 may then be translated relative to the outer tube 702, collapsing the members 706 towards each other. The blades 708 on the members 706 may then score the stent. The stent may be trimmed by the collapsing bladed members 706 and/or by additional rotational force of the inner tube 704.

Figure 8:
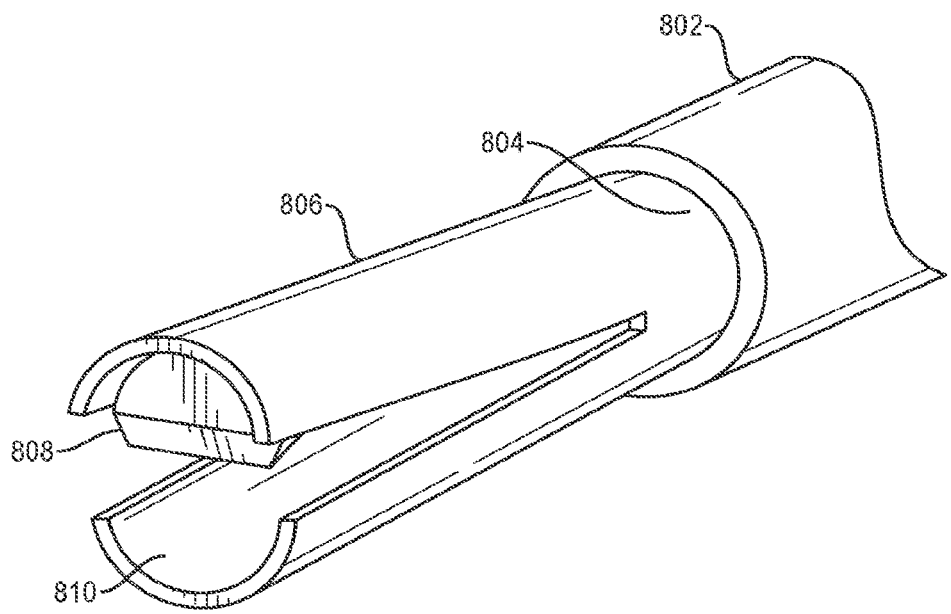
FIG. 8 illustrates an example embodiment of a medical device for trimming a stent.

Referring to FIG. 8, an embodiment of the disclosure may include an outer tube 802 with an inner tube 804 that may movably translate into and relative to the outer tube 802. The inner tube 804 may have two arms 806 splayed at its distal end. The two arms 806 may include one or more sharpened edges, e.g., blades 808, that is/are directed inwardly. The splayed members 806 will close towards each other when the inner tube 804 is translated proximally through the outer tube 802. In the inner tube's 804 closed state, a window 810 is vacant to allow for the device 800 to be guided along a guidewire (not shown). When the device 800 reaches the stent (not shown), the inner tube 804 may be translated through the outer tube 802 distally so that the members 806 splay open to receive an excess portion of the stent. The inner tube 804 may then be translated proximally, collapsing the members 806 towards each other. The one or more blades 808 on the members 806 may then score the stent. The stent may be trimmed by the collapsing bladed members 806 or by additional rotational force of the inner tube 804.

Figure 9:
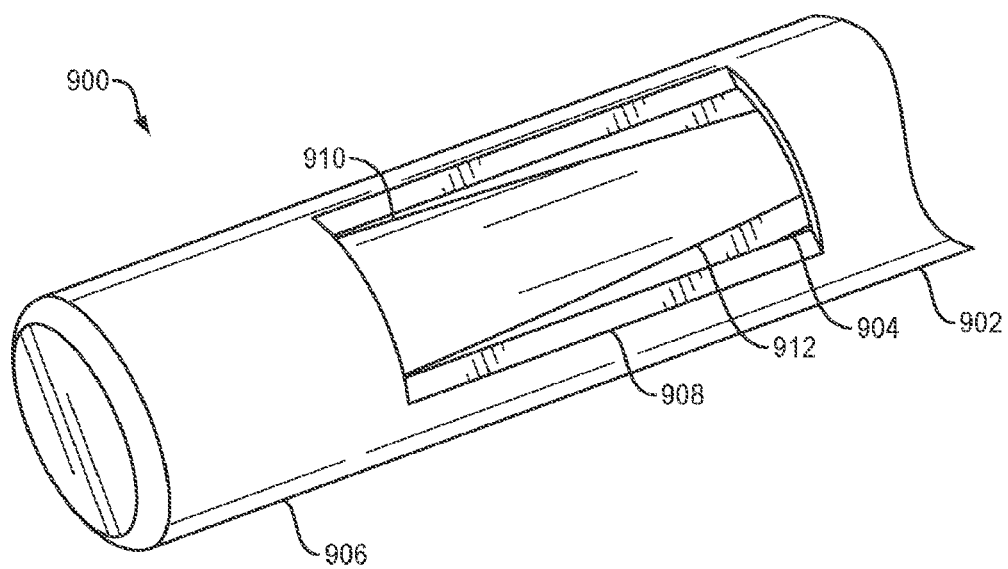
FIG. 9 illustrates an example embodiment of a medical device for trimming a stent.

Referring to FIG. 9, an example embodiment of the disclosure may include an outer tube 902 with an inner tube 904 that may slide into the outer tube 902. The outer tube 902 may have a rigid tip 906 with a window 908. The inner tube 904 may have a cutout 910 with at least one edge 912 along the cutout 910. When the cutout 910 is aligned with the window 908, a guidewire and/or a stent may pass through the device 900 (not shown). A medical professional may trim an excess portion of stent by rotating the inner tube 904 relative to the outer tube 902. The stent is trimmed by an edge 912 of the cutout 910 compressing the stent against the border of the window 908. The excess stent may be withdrawn from the stent placement site by withdrawing the inner tube 902 or the entire device 900.

Figure 10A:
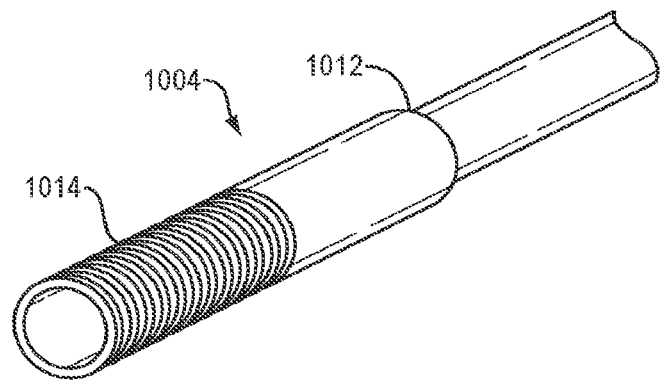
FIG. 10A illustrates an inner tube of an example embodiment of a medical device for trimming a stent.
Figure 10B:
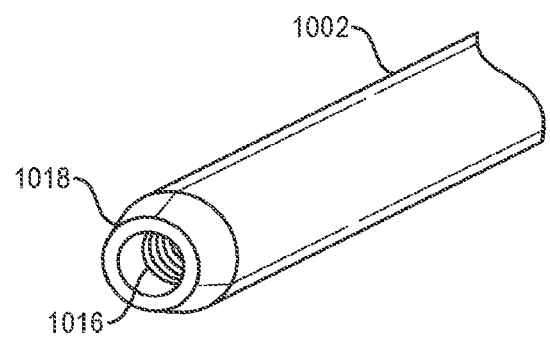
FIG. 10B illustrates an outer tube of an example embodiment of a medical device for trimming a stent.
Figure 10C:
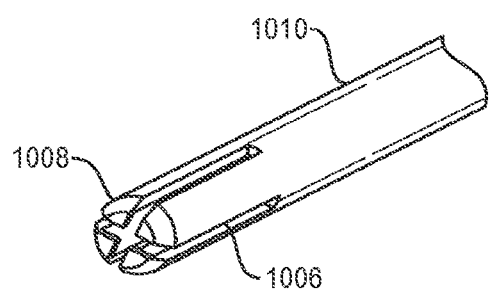
FIG. 10C illustrates a third tube of an example embodiment of a medical device for trimming a stent.

Referring to FIGS. 10A-10C, an example embodiment of the disclosure may include an inner tube 1004 that may have a concentric internal shelf 1012 on the inside of the inner tube 1004 of a smaller diameter than the inner tube 1004. The inner tube 1004 may include outer threads 1014 on its distal end. An embodiment may also include an outer tube 1002 that may have inner threads 1016 at its distal end that engage the outer threads 1014 of the inner tube 1004. The outer tube 1002 may taper down to a smaller diameter at a distal end 1018. An embodiment may include a bladed tube 1010 that may split into concentric fingers 1006. The distal end of the bladed tube 1010 may include blades that may be concentrically spaced apart.

Figure 11A:
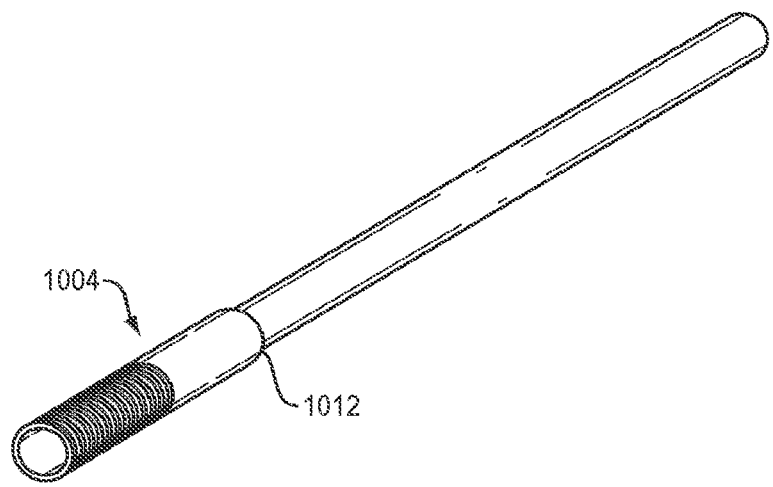
FIG. 11A illustrates an inner tube of an example embodiment of a medical device for trimming a stent.
Figure 11B:
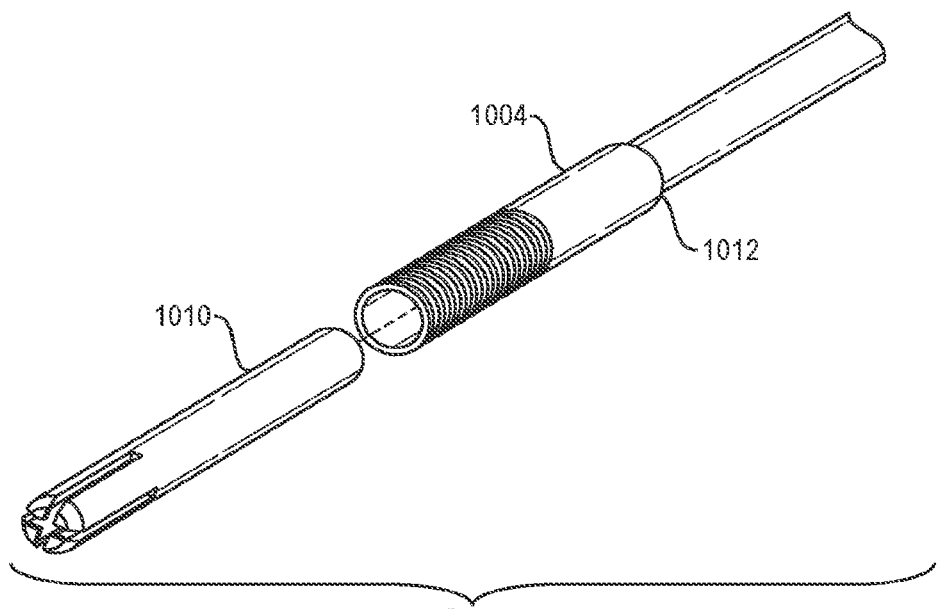
FIG. 11B illustrates an inner tube and a third tube of an example embodiment of a medical device for trimming a stent.
Figure 11C:
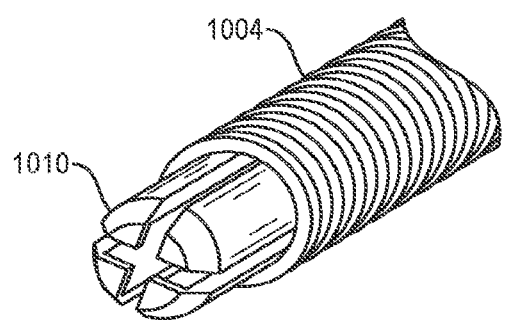
FIG. 11C illustrates an assembly of the components of FIGS. 11A and 11B.
Figure 11D:
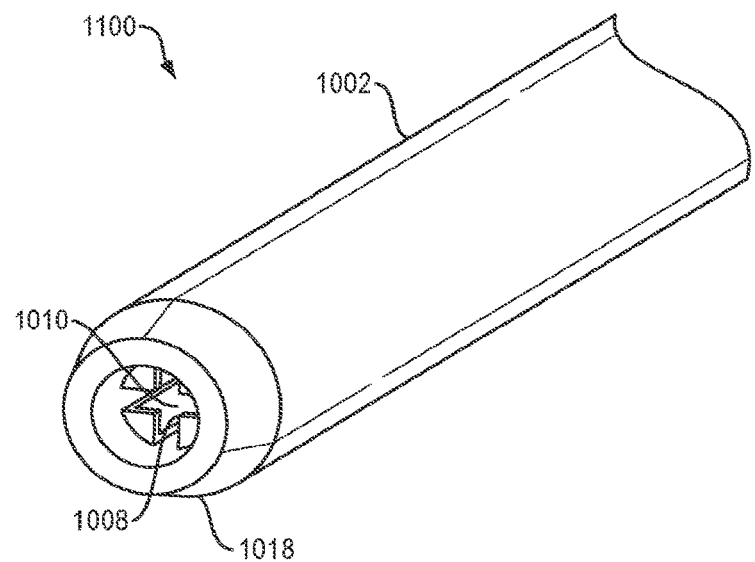
FIG. 11D illustrates an outer tube added to the assembly of FIG. 11C.
Figure 11E:
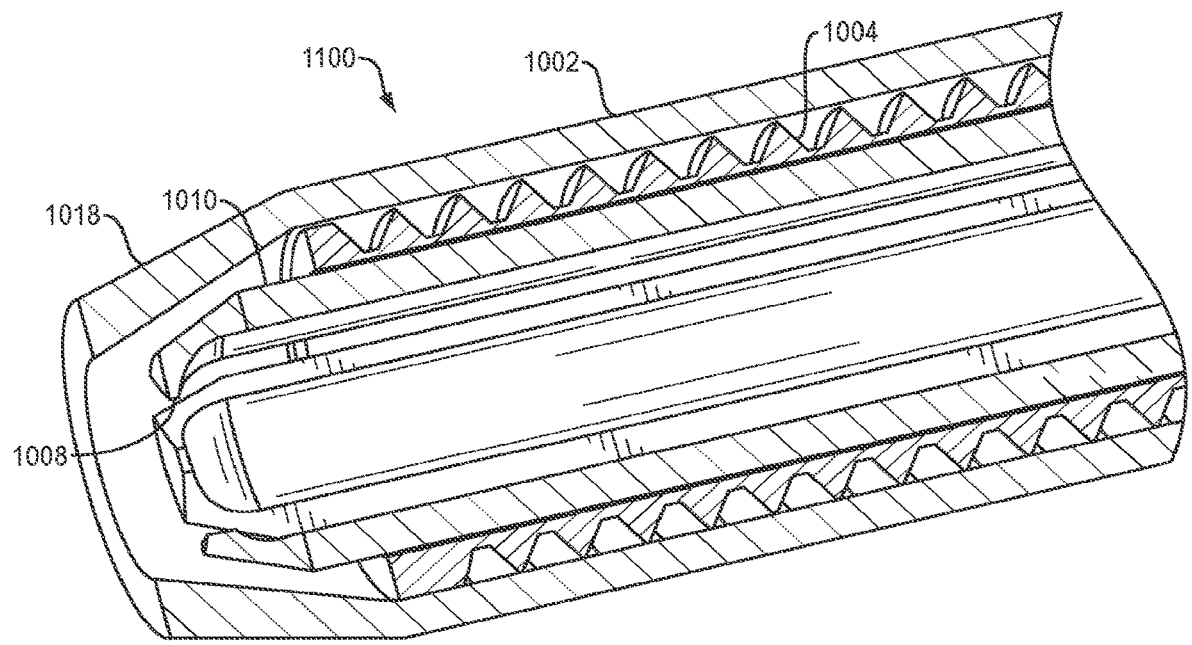
FIG. 11E illustrates a cross-sectional view of the assembly of FIG. 11D.

Referring to FIGS. 11A-11E, bladed tube 1010 may slide into inner tube 1004 until it is stopped by the internal shelf 1012. FIG. 11C illustrates the combination of the bladed tube 1010 slid into the inner tube 1004. This assembly shown in FIG. 11C may be screwed into the outer tube 1002, as shown in FIGS. 11D and 11E. The three tubes result in a device 1100 that is ready to receive a stent for trimming. The bladed tube 1010 may receive a stent while within the inner tube 1004 and the outer tube 1002, or a stent may be passed through device 1100 from its proximal end and out of its distal end. A medical professional may measure at what point the stent should be trimmed by moving the distal end of device 1100 along the stent. To trim the stent, the inner tube 1004 may be rotated while inside the outer tube 1002 so that the outer threads 1014 engage the inner threads 1016. Alternatively, the outer tube 1002 may be rotated against the inner tube 1004, or the tubes may be rotated against each other to engage the threads. As the threads are engaged, the inner tube 1004 will be driven distally within the outer tube 1002. The bladed tube 1010 will also be driven distally within the outer tube 1002 as the inner shelf 1012 pushes the bladed tube 1010 as the inner tube 1004 moves distally. The bladed tube 1010 will move distally until it reaches the tapered distal end 1018 of the outer tube 1002, at which point the blades 1008 will be compressed radially towards the center of the bladed tube 1010.

This blade compression trims the stent at the desired location in vivo. While the threads of the tubes provide control and prevent accidental trimming of the stent while in use, an alternative embodiment may trim the stent by compressing the inner tube 1004 containing the bladed tube 1010 against the taper 1018 without the use of threads 1014 and 1016. This would be achieved by pulling the outer tube 1002 proximally against the inner tube 1004, and collapsing the blades 1008. An embodiment may include a protective tubular sheath that covers the blades 1008 and protects the stent. The sheath may be retracted prior to trimming the stent.

Figure 12:
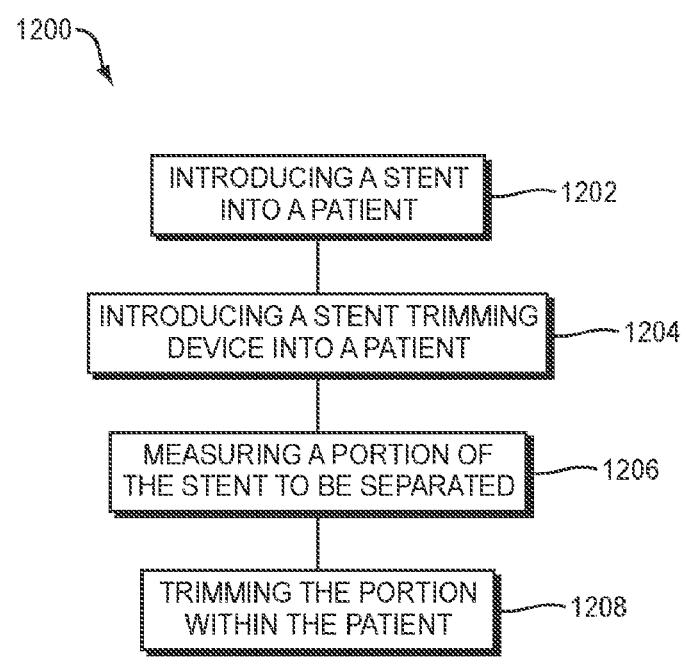
FIG. 12 is a diagram of a method for trimming a stent.

Referring to FIG. 12, a method 1200 of using one or more of the above or other various embodiments of the present disclosure may include a medical professional who may introduce 1202 a stent into a patient. The medical professional may introduce 1204 a stent trimming device embodiment of the disclosure into the patient. Alternatively, the trimming device may be introduced 1204 at the same time as the stent 1202. The medical professional may measure 1206 a portion of the stent to be trimmed. The medical professional may trim 1208 the portion to be trimmed within the patient. The medical professional may withdraw the portion and the device from the patient.

Devices according to the embodiments described, and in accordance with other embodiments of the present disclosure, alone or in a system or kit or as part of a method or procedure, including with other accessories, may be used in cavities, lumens, tracts, vessels and organs of the body, aside from stenting the ureter, such as procedures to drain, access or otherwise treat or diagnose conditions in the peritoneal, abdominal, bronchial or thoracic cavities, vascular vessels, gastrointestinal or urinary tract, uterus, bladder, lung and liver organs, etc.

What is claimed is:

1. A device for trimming a proximal end of a stent to a desired length, comprising:
    an outer tube; and
    an inner tube having a proximal end, a distal end, and an inner diameter configured to receive an outer diameter of at least a portion of the proximal end of the stent in excess of the desired length, the inner tube movably disposed within the outer tube, the distal end of the inner tube including an end effector configured to trim the portion from the stent while the device and stent are within a patient,
wherein the end effector has an opened and closed configuration, and
    wherein the end effector has two or more arms biased away from a longitudinal axis of the device in the opened position.

2. A device for trimming a proximal end of a stent to a desired length, comprising:
    an outer tube; and
    an inner tube movably disposed within the outer tube, the inner tube having a proximal end and a distal end, the distal end configured to trim a portion of the proximal end of the stent in excess of the desired length in vivo; and
        (a) wherein the device further comprises a tip extended from a distal end of the outer tube, the tip including a window having an opening along a side surface of the outer tube substantially perpendicular to a longitudinal axis of the outer tube, the window configured to receive at least the portion of the stent; and a sharpened edge at the distal end of the inner tube, whereby relative movement of the inner tube with respect to the outer tube engages the sharpened edge with the tip or (b) wherein the device further comprises a pair of inner arms extended from the distal end of the inner tube and biased toward each other in the direction of the longitudinal axis, each with a first inward facing tab with a pair of notches; and a pair of outer arms extended from the outer tube and biased toward each other in the direction of the longitudinal axis, each with a pair of second inward facing tabs configured to engage a notch on the first inward facing tabs of each inner arm on opposing sides of the inner tube or (c) wherein the device further comprises a first aperture near a distal end of the outer tube that is substantially perpendicular to a longitudinal axis of the outer tube; and a second aperture near the distal end of the inner tube that is substantially perpendicular to a longitudinal axis of the inner tube with at least one sharp edge, the inner tube and outer tube being rotatable with respect to each other to engage the inner tube edge or (d) wherein the inner tube has a concentric internal shelf on the inside of the inner tube of a smaller diameter than the inner tube and further comprising a third tube removably disposed within the distal end of the inner tube, the third tube including an opening configured to receive at least the portion of the stent to be trimmed and a plurality of blades at a distal end of the third tube that are concentrically spaced apart from each other around the opening, and wherein the outer tube tapers down to a smaller diameter at a distal end.

3. The device of claim 2, wherein the device further comprises:
    a tip extended from a distal end of the outer tube, the tip including a window having an opening along a side surface of the outer tube substantially perpendicular to a longitudinal axis of the outer tube, the window configured to receive at least the portion of the stent; and
    a sharpened edge at the distal end of the inner tube, whereby relative movement of the inner tube with respect to the outer tube engages the sharpened edge with the tip.

4. The device of claim 3, wherein the tip includes a post disposed within the tip, the post having a beveled proximal face angled toward the window opening.

5. The device of claim 2, wherein the device further comprises:
    a pair of inner arms extended from the distal end of the inner tube and biased toward each other in the direction of the longitudinal axis, each with a first inward facing tab with a pair of notches; and
    a pair of outer arms extended from the outer tube and biased toward each other in the direction of the longitudinal axis, each with a pair of second inward facing tabs configured to engage a notch on the first inward facing tabs of each inner arm on opposing sides of the inner tube.

6. The device of claim 5, further comprising a pair of fingers extending inwardly from the pair of outer arms.

7. The device of claim 2, wherein the distal end of the inner tube comprises three splayed arms, each with a sharpened edge pointed substantially inward toward a longitudinal axis of the inner tube.

8. The device of claim 2, wherein the device further comprises:
    a first aperture near a distal end of the outer tube that is substantially perpendicular to a longitudinal axis of the outer tube; and
    a second aperture near the distal end of the inner tube that is substantially perpendicular to a longitudinal axis of the inner tube with at least one sharp edge, the inner tube and outer tube being rotatable with respect to each other to engage the inner tube edge.

9. The device of claim 2, wherein the inner tube has a concentric internal shelf on the inside of the inner tube of a smaller diameter than the inner tube and further comprising a third tube removably disposed within the distal end of the inner tube, the third tube including an opening configured to receive at least the portion of the stent to be trimmed and a plurality of blades at a distal end of the third tube that are concentrically spaced apart from each other around the opening, and wherein the outer tube tapers down to a smaller diameter at a distal end.

10. The device of claim 9, wherein the inner tube has outer threads on an outer surface at the distal end of the inner tube and wherein the outer tube has inner threads on an inner surface at the distal end of the outer tube that engage the outer threads on the inner tube.

11. A method of trimming a stent comprising:
   introducing a stent into a patient;
   introducing a stent trimming device into the patient;
   measuring a portion of the stent to be trimmed; and
   trimming the portion within the patient with the stent trimming device,
   wherein introducing the stent and introducing the stent trimming device are performed simultaneously.

12. The method of claim 11, wherein trimming the portion is performed by moving an inner tube relative to an outer tube of the device.

* * * * *